United States Patent [19]

Burley et al.

[11] 4,181,671
[45] Jan. 1, 1980

[54] NOVEL ORGANOTIN STABILIZER COMPOSITIONS

[75] Inventors: Joseph W. Burley, Wallasey; Ronald E. Hutton, Southport; Vincent Oakes, Eccleston, all of England

[73] Assignee: Akzo N.V., Arnhem, Netherlands

[21] Appl. No.: 912,729

[22] Filed: Jun. 5, 1978

Related U.S. Application Data

[63] Continuation of Ser. No. 742,071, Nov. 15, 1976, Pat. No. 4,134,878.

[30] Foreign Application Priority Data

Nov. 25, 1975 [GB] United Kingdom ............... 48390/75

[51] Int. Cl.$^2$ ............................................. C07F 7/22
[52] U.S. Cl. ............................ 260/410.6; 260/45.75 S; 260/414; 260/429.7
[58] Field of Search ..................... 260/429.7, 45.75 S, 260/410.6, 414

[56] References Cited

U.S. PATENT DOCUMENTS 3,803,083  4/1974  Brecker .......................... 260/45.75 S

*Primary Examiner*—V. P. Hoke
*Attorney, Agent, or Firm*—Stevens, Davis, Miller & Mosher

[57] ABSTRACT

A stabilizer composition for a polymer is described, said composition comprising a chemically combined structure of the formula

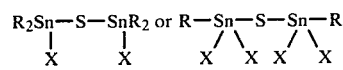

wherein R is a group having the formula

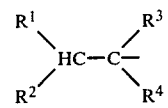

wherein $R^1$, $R^2$, $R^3$ and $R^4$ are independently a hydrogen atom, or an alkyl or substituted alkyl group having 1 to 18 carbon atoms, with the proviso that at least one of $R^1$ and $R^2$ contains adjacent to the group HC- a carbonyl group which forms a part of an acid group, ester group, acid halide group, ketone group or aldehyde group; and X is $-S(CH_2)_y-COOR^5$ or $-S(CH_2)_y-OCOR^5$, wherein y is 1 or 2, or $-SR^5$, $-OCOR^5$ or $-OCOCH=CHCOOR^5$, $R^5$ being an alkyl or substituted alkyl group having 1 to 18 carbon atoms.

5 Claims, No Drawings

NOVEL ORGANOTIN STABILIZER COMPOSITIONS

This is a continuation of application Ser. No. 742,071 filed Nov. 15, 1076 now U.S. Pat. No. 4,134,879 issued Jan. 16, 1979.

The present invention relates to synergistic organotin stabilizer compositions for polymers and to polyvinyl resins stabilized therewith, such as polyvinylchloride, polyvinylidene chloride and copolymers thereof.

One class of organotin stabilizers for polymers, particularly polyvinyl chloride and copolymers thereof, is described in U.S. applications Ser. No. 613,434 filed Sept. 15, 1975 and Ser. No. 660,631 filed Feb. 23, 1976.

This disclosed new class of stabilizer compounds has the following general formula:

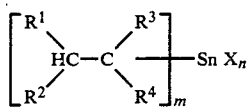
(a)

wherein $m+n=4$ and m is either 1 or 2; $R^1$, $R^2$, $R^3$ and $R^4$ are each independently a hydrogen atom, or an alkyl or substituted alkyl group having from 1 to 18 carbon atoms with the proviso that at least one of $R^1$ and $R^2$ contains adjacent to the group HC— a carbonyl group which forms a part of an acid group, ester group, aldehyde group, acid halide group or ketone group; X is a $-S(CH_2)_y-COOR^5$ or $-S(CH_2)_y-OCOR^5$ wherein y is 1 or 2 or a $-SR^5$, $-OCOR^5$ or $-OCOCH=CHCOOR^5$, $R^5$ being an alkyl group having 1 to 18 carbon atoms.

It is an object of this invention to provide an improved stabilizer composition for polyvinyl resins containing a compound of formula (a). Another object of the invention is to provide polyvinyl resins having improved light and heat stability. A more specific object of the invention is to improve the heat and light stability of polyvinyl resins with a novel composition containing as one of its components a compound of formula (a).

It has now been found that the heat and light stability of polyvinyl resins is improved in a synergistic manner if, in addition to one or more of the organotin compounds of formula (a), the composition also contains one or more of a certain class of organotin sulfides.

Accordingly, the invention provides a stabilizer composition which contains a synergistic combination of an organotin compound having the formula (a) as above defined, and an organotin sulfide having the formula:

(b)

wherein n is 2 to 10 and R is an alkyl group having from 1 to 18 carbon atoms or the group

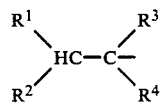

wherein $R^1$, $R^2$, $R^3$ and $R^4$ are as above defined for formula (a).

The organotin compounds of formula (a) may be prepared by the methods described in our co-pending patent applications referred to above. In these methods, the corresponding organotindihalides and trihalides are first produced as intermediate products which are subsequently reacted by common techniques to substitute the organic residue X for the halide.

The organotin sulfides of formula (b) in which R is an alkyl group are known stabilizers which may be prepared by such methods as those described in the U.S. Pat. Nos. 3,654,222 and 3,769,263.

The organotin sulfides of formula (b) wherein R is the group

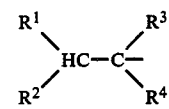

may be prepared in an analogous manner from the corresponding dihalides and trihalides, which occur as intermediate products in the preparation of the formula (a) compounds.

Alternatively, the synergistic combination of a compound of formula (a) with a sulfide of formula (b) may be formed in situ by simultaneously reacting the aforesaid dihalides or trihalides with the sulfur and X substituting species. At least a part of the synergistic combination may then be present as a chemically combined structure exemplified by

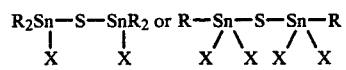

wherein R is as defined above.

In terms of compounds of formulae (a) and (b), the above in situ formed structures may be viewed as a chemical combination of one mole of $R_2SnX_2$ with one mole of $R_2SnS$ giving one mole of $R_4Sn_2SX_2$, or of four moles of $RSnX_3$ with one mole of $(RSnS_{1.5})_2$ giving three moles of $R_2Sn_2SX_4$.

Polyvinyl resins may be stabilized by incorporating therein an effective amount of the synergistic stabilizer composition of the present invention.

Generally, amounts of up to and including 5 wt.% calculated on the weight of the resin are sufficiently adequate for the purpose and effective stabilization is usually achieved with amounts in the range of 0.5 to 3 wt.% calculated on the weight of the resin. The present invention includes within its scope all polyvinyl resins, i.e., resins containing $-CH:CH_2$ groups in polymerized form, such as polyvinyl chloride and polyvinyl chloride-acetate and the like, stabilized by the incorporation therein of the aforementioned synergistic stabilizer compositions.

The preparation of novel organotin sulfides of formula (b) wherein R is a group as hereinbefore defined is illustrated in the two following specific Examples:

EXAMPLE I 434 g of sodium sulfide trihydrate dissolved in 150 ml of water was added to 75 g of $C_4H_9OCOCH_2CH_2SnCl_3$ dissolved in 150 ml of toluene contained in a three neck flask. After stirring for one hour at 60° C. the toluene phase was separated from the aqueous phase and evaporated to leave 62.3 g of a yellow solid, which was shown by analysis to be $(C_4H_9OCOCH_2CH_2SnS_{1.5})_2$.

EXAMPLE II 80.8 g of sodium sulfide nonahydrate dissolved in 200 ml of water was added to 150 g of $(C_4H_9OCOCH_2CH_2)_2$ Sn $Cl_2$ dissolved in 200 ml of tetrahydrofuran. The mixture was stirred at 60° C. for a period of 30 minutes and the non-aqueous layer separated from the water phase. Evaporation of the tetrahydrofuran phase yielded 134.5 g of a pale yellow viscous liquid, which was shown by analysis to be $(C_4H_9OCOCH_2CH_2)_2$ SnS.

In the following tables the synergistic effect of the stabilizer combinations of the present invention is demonstrated on samples of polyvinyl chloride resin. The effect is demonstrated in terms of heat stability and rated visually as a color change which occurs on exposing the samples to an oven temperature of 185° C. at increasing lengths of time.

The numerical ratings given corresponding to the following color scale:

1—colorless
2—very pale yellow
3—pale yellow
4—yellow
5—dark yellow
6—orange
7—pale brown
8—brown
9—dark brown
10—black

Table I

Stabilizer content: 1 wt.% of R $SnX_3$ or R $SnX_3$ (0.9) + organotin sulfides (0.1)
$R = C_4H_9OCOCH_2CH_2-$ and $X =$ iso octyl thioglycollate

| Time at 185° (min) | organotin sulfide added | | | | |
|---|---|---|---|---|---|
| | R $SnX_3$ | $(C_4H_9SnS_{1.5})_n$ | $(C_4H_9)_2SnS$ | (R $SnS_{1.5})_n$ | $R_2Sn$ S |
| 10 | 1 | 1 | 1 | 1 | 1 |
| 20 | 1 | 1 | 1 | 1 | 1 |
| 30 | 2 | 1 | 1 | 1 | 1 |
| 40 | 5 | 3 | 1 | 3 | 2 |
| 45 | 10 | 10 | 10 | 10 | 10 |

Table II

Stabilizer content: 1 wt.% of $R_2$ Sn $X_2$ or $R_2$ $SnX_2$ (0.9) + organotin sulfide (0.1)
R and X as in Table I.

| Time at 185° (min) | organotin sulfide added | | | | |
|---|---|---|---|---|---|
| | $R_2$ $SnX_2$ | $(C_4H_9SnS_{1.5})_n$ | $(C_4H_9)_2SnS$ | (R Sn $S_{1.5})_n$ | $R_2Sn$ S |
| 10 | 1 | 1 | 1 | 1 | 1 |
| 20 | 1 | 1 | 1 | 1 | 1 |
| 30 | 1 | 1 | 1 | 1 | 1 |
| 40 | 2 | 2 | 2 | 2 | 2 |
| 45 | 10 | 4 | 8 | 10 | 8 |
| 50 | | 10 | 10 | | 10 |

Table III

Stabilizer content: 2 wt.% total of R Sn $X_3$ and/or $(C_4H_9Sn$ $S_{1.5})_n$ as indicated
$R = CH_3OCOCH_2CH_2-$ and $X =$ iso octyl thio glycollate

| Time at 185° | Amount of organotin sulfide present | | | |
|---|---|---|---|---|
| | 0 | 1.2 | 1.6 | 2.0 |
| 10 | 1 | 1 | 2 | 3 |
| 20 | 1 | 1 | 2 | 3 |
| 30 | 1 | 1 | 2 | 4 |
| 40 | 10 | 3 | 4 | 8 |
| 50 | | 8 | 7 | 9 |
| 60 | | 10 | 8 | 10 |
| 70 | | | 10 | |

Table IV

Stabilizer content: 2 wt.% total of R Sn $X_3$ and/or $(C_4H_9)_2Sn$ S as indicated
R and X as in Table III

| Time at 185° | Amount of organotin sulfide present | | | |
|---|---|---|---|---|
| (min) | 0 | 0.8 | 1.6 | 2.0 |
| 20 | 1 | 1 | 1 | 2 |
| 40 | 10 | 1 | 2 | 4 |
| 60 | | 3 | 3 | 7 |
| 80 | | 10 | 7 | 8 |
| 100 | | | 8 | 9 |
| 110 | | | 10 | 10 |

Table V

Stabilizer content: 2 wt.% total of $R_2$ Sn $X_2$ and/or $(C_4H_9SnS_{1.5})_n$ as indicated
R and X as in Table III

| Time at 185° | Amount of organotin sulfide present | | | | |
|---|---|---|---|---|---|
| (min) | 0 | 0.2 | 0.4 | 1.0 | 2.0 |
| 20 | 1 | 1 | 1 | 1 | 3 |
| 40 | 2 | 2 | 2 | 2 | 5 |
| 60 | 2 | 2 | 2 | 3 | 10 |
| 80 | 3 | 3 | 3 | 7 | |
| 90 | 6 | 4 | 7 | 9 | |
| 100 | 10 | 9 | 8 | 10 | |
| 110 | | 10 | 10 | | |

Table VI

Stabilizer content: 2 wt.% total of $R_2Sn$ $X_2$ and/or $(C_4H_9)_2Sn$ S as indicated
R and X as in Table III

| Time at 185° | Amount of organotin sulfide present | | | | |
|---|---|---|---|---|---|
| (min) | 0 | 0.4 | 0.8 | 1.4 | 2.0 |
| 20 | 1 | 1 | 1 | 2 | 2 |

Table VI-continued

Stabilizer content: 2 wt.% total of $R_2Sn\ X_2$ and/or $(C_4H_9)_2Sn\ S$ as indicated
R and X as in Table III

| Time at 185° (min) | Amount of organotin sulfide present | | | | |
|---|---|---|---|---|---|
| | 0 | 0.4 | 0.8 | 1.4 | 2.0 |
| 40 | 1 | 1 | 2 | 2 | 3 |
| 60 | 2 | 2 | 2 | 3 | 4 |
| 80 | 4 | 3 | 3 | 7 | 5 |
| 90 | 10 | 9 | 7 | 7 | 8 |
| 100 | | 10 | 8 | 8 | 9 |
| 110 | | | 10 | 10 | 10 |

While the data presented in Tables I to VI relates to the use of synergistic stabilizer combinations prepared by mixing separate organotin compounds of formulae (a) and (b), similar results are obtained with combinations which are formed by in situ preparation. The alternative in situ preparation of synergistic combinations is illustrated in the next two Examples.

EXAMPLE III 81.6 g of iso-octylthioglycollate, 70.8 g of $C_4H_9OCOCH_2CH_2SnCl_3$ and 150 ml of toluene were stirred in a three neck flask and a solution of 13.2 g of sodium sulfide trihydrate and 16 g of sodium hydroxide in 150 ml of water was slowly added thereto. Stirring was continued for one hour, whereafter the toluene phase separated from the aqueous phase. On evaporating the toluene phase 133 g of an amber liquid remained which was shown by analysis to have the structure:

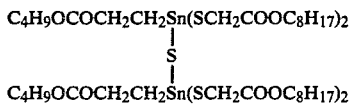

EXAMPLE IV 40.9 g of iso-octylthioglycollate, 89.5 g of $(C_4H_9OCOCH_2CH_2)_2SnCl_2$ and 150 ml of toluene were stirred in a three neck flask and a solution of 13.2 g sodium sulfide trihydrate and 8 g of sodium hydroxide in 150 ml of water was slowly added thereto. After continued stirring for one hour, the toluene phase was separated from the aqueous phase and evaporated to yield 119 g of an amber liquid, which was shown by analysis to have the structure:

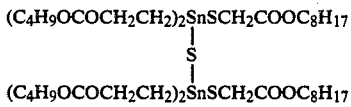

In Examples III and IV almost stoichiometric quantities of reactants were used giving almost quantitative yields of products having the structure indicated. While these products may be directly used as useful synergistic combinations they may, of course, be further combined with separate compounds of formulae (a) and (b). In fact, these further combinations may also be obtained directly by altering the relative molar quantities of the glycollate and sulfide in the experimental procedure of these Examples.

Although the invention is described in detail for the purpose of illustration, it is to be understood that such detail is solely for that purpose and that variations can be made therein by those skilled in the art without departing from the spirit and scope of the invention except as it may be limited by the claims.

What is claimed is:

1. A stabilizer composition for a polymer, said composition comprising a chemically combined structure of the formula

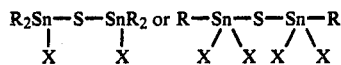

wherein R is a group having the formula

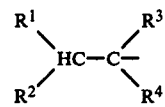

wherein $R^1$, $R^2$, $R^3$, and $R^4$ are independently a hydrogen atom, or an alkyl or substituted alkyl group having 1 to 18 carbon atoms, with the proviso that at least one of $R^1$ and $R^2$ contains adjacent to the group HC— a carbonyl group which forms a part of an acid group, ester group, acid halide group, ketone group, or aldehyde group; and X is —$S(CH_2)_y$—$COOR^5$ or —$S(CH_2)_y$—$OCOR^5$, wherein y is 1 or 2, or —$SR^5$, —$OCOR^5$ or —$OCOCH=CHOOR^5$, $R^5$ being an alkyl or substituted alkyl group having 1 to 18 carbon atoms.

2. A stabilizer composition for a polymer, said composition comprising a chemically combined structure of the formula

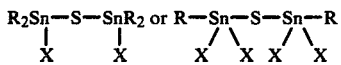

wherein R is a group having the formula

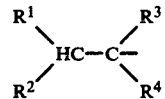

wherein $R^1$, $R^2$, $R^3$, and $R^4$ are independently a hydrogen atom, or an alkyl or substituted alkyl group having 1 to 18 carbons atoms, with the proviso that at least one of $R^1$ and $R^2$ contains adjacent to the group HC— a carbonyl group which forms a part of an acid group, ester group, acid halide group, ketone group, or aldehyde group; and X is —$S(CH_2)_y$—$COOR^5$ or —$S(CH_2)_y$—$OCOR^5$, wherein y is 1 or 2, or —$SR^5$, —$OCOR^5$ or —$OCOCH=CHCOOR^5$, $R^5$ being an alkyl or substituted alkyl group having 1 to 18 carbon atoms, wherein said composition is prepared by reacting an organotin halide having the formula

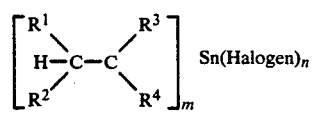

wherein m+n=4 and m is 1 or 2, and $R^1$, $R^2$, $R^3$, and $R^4$ have the same meaning as above; simultaneously with a reactant for substituting a sulfur atom for halogen and a reactant for substituting X for halogen, wherein X is as defined above.

3. The stabilizer composition of claim 2 wherein the reaction is conducted in a mixture of reactants containing an excess of the reactant for substituting a sulfur atom for halogen.

4. The stabilizer composition of claim 2 wherein the said reaction is conducted in a mixture containing stoichiometric amounts of the three reactants and the chemical reaction is effected substantially to completion whereby no significant amount of any of the reactants remains.

5. The stabilizer composition of claim 2 wherein the reaction is conducted in a mixture of the reactants containing an excess of the said reactant for substituting X for halogen.

* * * * *